US011980502B2

(12) United States Patent
Correales et al.

(10) Patent No.: US 11,980,502 B2
(45) Date of Patent: May 14, 2024

(54) HARMONIC SHEAR WAVE IMAGING

(71) Applicant: The Penn State Research Foundation, University Park, PA (US)

(72) Inventors: Daniel Humberto Cortes Correales, State College, PA (US); Che-Yu Lin, Taoyuan (TW); Seyedali Sadeghi, Malden, MA (US)

(73) Assignee: The Penn State Research Foundation, University Park, PA (US)

( * ) Notice: Subject to any disclaimer, the term of this patent is extended or adjusted under 35 U.S.C. 154(b) by 287 days.

(21) Appl. No.: 17/296,567

(22) PCT Filed: Nov. 25, 2019

(86) PCT No.: PCT/US2019/062911
§ 371 (c)(1),
(2) Date: May 25, 2021

(87) PCT Pub. No.: WO2020/112586
PCT Pub. Date: Jun. 4, 2020

(65) Prior Publication Data
US 2022/0022846 A1 Jan. 27, 2022

Related U.S. Application Data

(60) Provisional application No. 62/772,913, filed on Nov. 29, 2018.

(51) Int. Cl.
*A61B 8/08* (2006.01)
*G01S 7/52* (2006.01)

(52) U.S. Cl.
CPC .......... *A61B 8/485* (2013.01); *G01S 7/52022* (2013.01); *G01S 7/52042* (2013.01); *A61B 8/483* (2013.01)

(58) Field of Classification Search
CPC ..... A61B 8/485; A61B 8/482; G01S 7/52022; G01S 7/52042
See application file for complete search history.

(56) References Cited

U.S. PATENT DOCUMENTS 5,606,971 A * 3/1997 Sarvazyan ......... G01N 29/2456
600/587
5,810,731 A * 9/1998 Sarvazyan .......... G01S 15/8909
600/438

(Continued)

FOREIGN PATENT DOCUMENTS

JP 3664826 B2 * 6/2005 ......... G01N 29/0609

OTHER PUBLICATIONS

International Search Report dated Feb. 3, 2020; International Appl. No. PCT/US2019/062911.

(Continued)

*Primary Examiner* — Colin T. Sakamoto
(74) *Attorney, Agent, or Firm* — DINSMORE & SHOHL LLP

(57) ABSTRACT

A method of performing shear wave elastography in tissue includes transmitting successively a series of ultrasound push pulses in the tissue in a region of interest (ROI) using a single array transducer. The acoustic intensities of the push pulses are sinusoidally modulated with a modulation frequency, Each push pulse generates an acoustic radiation force that pushes the tissue and creates an individual shear wave propagating through the tissue. The amplitudes of the shear waves, and therefore, the displacements produced by the push pulses, are positively proportionally to the intensities of the push pulses. The successively created individual shear waves with different amplitudes sum together to form (Continued)

a continuous, harmonic summed shear wave with a single frequency the same as the modulation frequency of the push pulses.

14 Claims, 8 Drawing Sheets

(56) References Cited

U.S. PATENT DOCUMENTS

| | | | |
|---|---|---|---|
| 8,469,891 B2 | 6/2013 | Maleke et al. | |
| 8,602,994 B2 | 12/2013 | Zheng et al. | |
| 9,237,878 B2 | 1/2016 | Chen et al. | |
| 11,464,489 B2* | 10/2022 | Peterson | G01S 15/8915 |
| 2010/0286520 A1* | 11/2010 | Hazard | G01S 7/52071 |
| | | | 601/2 |
| 2011/0063950 A1* | 3/2011 | Greenleaf | G01S 7/52038 |
| | | | 367/87 |
| 2013/0072277 A1* | 3/2013 | Rosenau | G07F 17/3276 |
| | | | 463/16 |
| 2015/0216507 A1 | 8/2015 | Greenleaf et al. | |
| 2015/0265249 A1 | 9/2015 | Urban et al. | |
| 2019/0314002 A1* | 10/2019 | Peterson | G01S 7/52071 |
| 2021/0356434 A1* | 11/2021 | Chen | G01N 29/42 |

OTHER PUBLICATIONS

Sadeghi, S., Lin, C., and Cortes, D.H., "Narrowband Shear Wave Generation Using Sinusoidally Modulated Acoustic Radiation Force." IEEE Transactions on Ultrasonics, Ferroelectrics, and Frequency Control, vol. 66, No. 2, Dec. 5, 2018 (Dec. 5, 2018) [online] <URL: https://ieeexplore.ieee.org/abstract/document/8561188>.

Giannoula, A., and Cobbold, R.S.C., "Propagation of Shear Waves Generated by a Modulated Finite Amplitude Radiation Force in a Viscoelastic Medium." IEEE Transactions on Ultrasonics, Ferroelectrics, and Frequency Control, vol. 56, No. 3, Mar. 2009 (Mar. 3, 2009) (online] <URL: https://ieeexplore.ieee.org/document/4816065.

* cited by examiner

FIG. 5
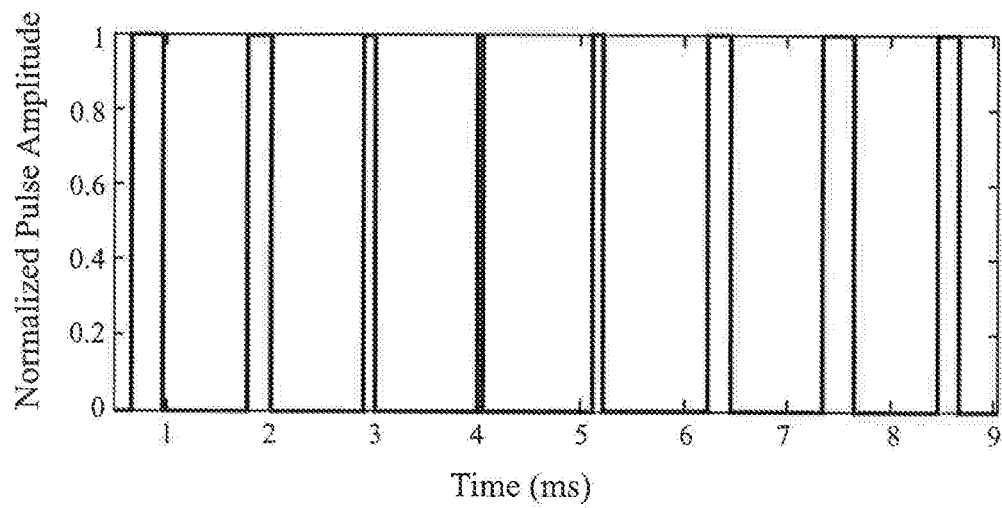
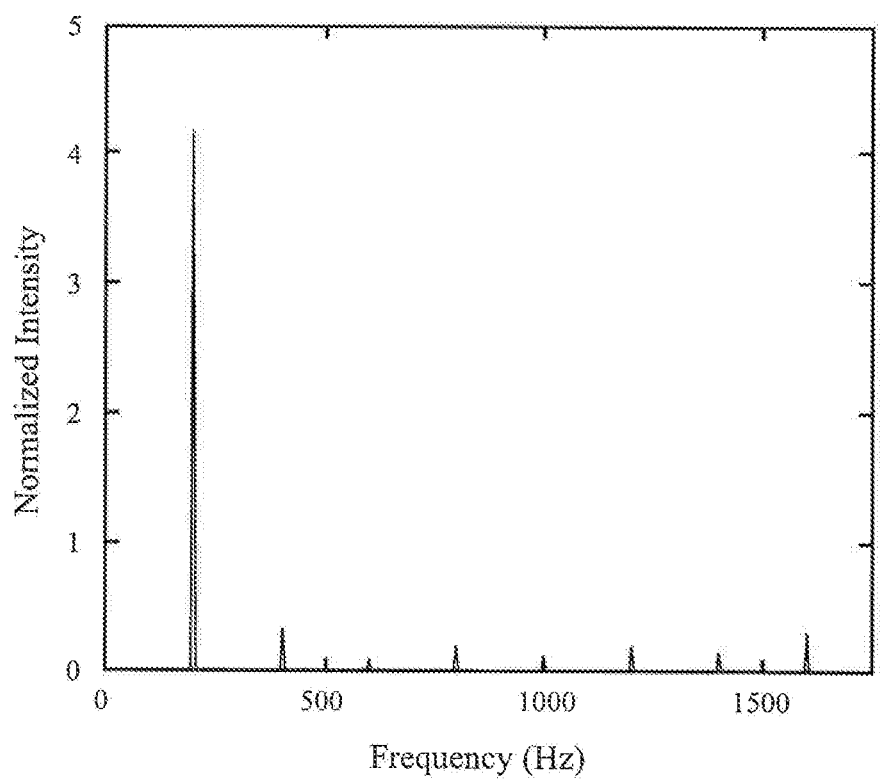
FIG. 6

FIG. 8A
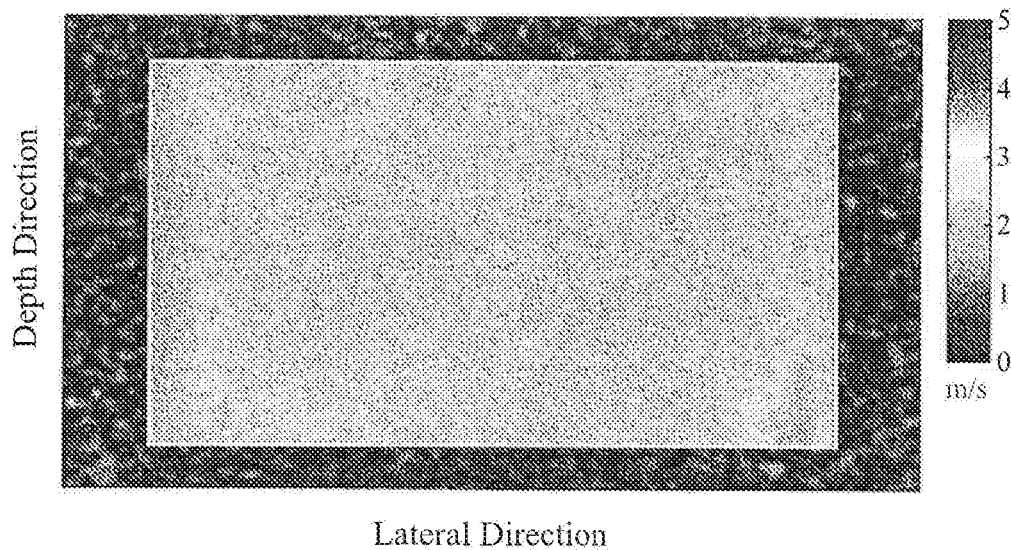
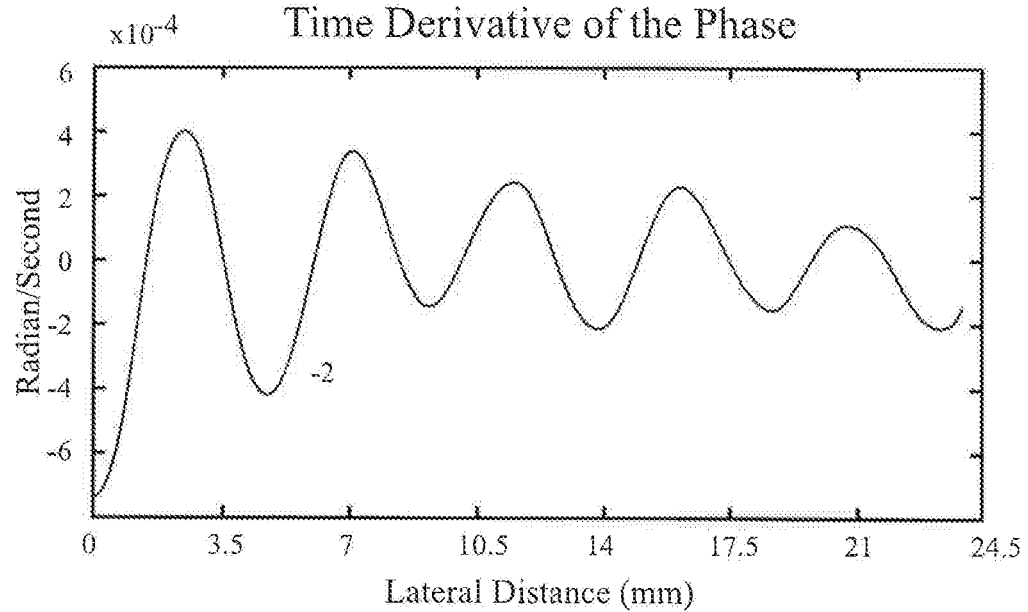
FIG. 8B

HARMONIC SHEAR WAVE IMAGING

CROSS REFERENCE TO RELATED APPLICATION

This application is the U.S. National Stage of PCT/US2019/062911 filed Nov. 25, 2019, which claims priority to U.S. Provisional Patent Application Ser. No. 62/772,913, filed Nov. 29, 2018, the entire content of both are incorporated herein by reference in their entirety.

FIELD OF THE INVENTION

The present invention relates to shear wave elastography in tissues.

BACKGROUND OF THE INVENTION

The shear modulus of soft tissues has important clinical implications since it often changes as a consequence of disease or injury. Therefore, the shear modulus can be a sensitive biomarker for diagnosing and monitoring a variety of clinical conditions. Elastography is a generic name given to methods for measuring the shear modulus non-invasively in the body. Elastography requires the generation of shear wave in the tissue of interest and measurement and analysis of the shear wave speed using an imaging method or other noninvasive techniques. The shear modulus and other viscoelastic properties of the tissues can be calculated based by analyzing the measurements of shear wave speed. Elastography can be further classified according to the temporal characteristics of the shear wave as transient or harmonic. Transient methods apply an impulsive short-duration acoustic or mechanical excitation to induce shear waves in the tissue and use the group velocity of the shear wave to evaluate the shear modulus of soft tissues. A drawback of transient methods is that factors such as ultrasound frequencies, transducer types, and imaging depths produce biases in the shear wave speed measurements. These biases can be explained, in part, by the effect of those parameters on the bandwidth of the transient shear waves. Therefore, these biases must be taken into account when defining thresholds of shear wave speed measurements. Harmonic methods, on the other hand, use shear waves having a single frequency (narrowband spectrum) to evaluate the shear modulus of soft tissues. The advantage of using harmonic methods is that the biases observed in transient methods could be reduced due to the narrowband spectral content of the induced harmonic shear wave. In harmonic methods, harmonic shear waves are often excited using an external mechanical driver, or a separate focused ultrasound transducer. An example of a harmonic elastography method is called magnetic resonance elastography (MRE). However, the need of a separate driver may not be optimal for clinical use because the added complexity to the measurement.

SUMMARY OF THE INVENTION

The present invention provides a method called Harmonic Shear Wave Imaging (HSWI) capable of generating narrowband shear waves and measuring shear wave speed using a single array transducer. The array transducer may be a linear, 1.5D or 2D clinical array transducer.

HSWI uses a set (part or the totality) of elements of the (linear, 1.5D or 2D) array transducer to transmit a series of ultrasound pulses ("push pulses") with different acoustic intensities. Each push pulse generates an acoustic radiation force that pushes the tissue and creates an individual shear wave propagating through the tissue. The acoustic intensity of the push pulses can be varied to follow a sinusoidally changing pattern. In an embodiment, different push pulse intensities are achieved with different push durations, and the shear wave created by a push pulse with a longer duration has a higher amplitude. The sinusoidal variation of intensity may also be produced by changing other parameters of the push pulse such as voltage, aperture size (i.e., number of elements in the array), and other approaches that will be clear to those of skill in the art. The displacement produced by each push pulse build up together to form a continuous, narrowband shear wave with a main frequency that can be controlled by the user. This controllable frequency is the same as that of the sinusoidal modulation frequency of the push pulses.

Push pulses are interleaved with imaging/detection pulses to measure and reconstruct maps of shear wave speed. The imaging pulses may be plane-wave, which allow measuring displacements in a region of the tissue of interest. However, other types of detection pulses can also be used. Applying imaging/detection pulses between push pulses allows generating and measuring shear wave propagation simultaneously.

By estimating the wavelength λ of the narrowband resulting shear wave with a known frequency f, the shear wave speed $v_s$ can be calculated by the relationship:

$$v_s = f\lambda$$

The shear wave speed map of the region of interest can then be constructed.

The range of the controllable frequency is broad, for example, from 50 up to 600 Hz. The measured shear wave speed obtained with the present method can be directly compared to those obtained with other harmonic shear wave elastography (SWE) methods. Additionally, since the present method produces a sinusoidal excitation at a single frequency that can be set to be the same as MRE, the results of the present method and MRE are comparable. Since the range of the controllable frequency is broad, the present method is useful to measure not only the stiffness but also the viscoelastic properties of the tissues. HSWI is appropriate for clinical practice because only a single clinical transducer is needed to induce and monitor the shear wave.

According to the embodiments of the present invention, continuous harmonic shear waves with a single and controllable frequency can be produced in the tissue. The intensity of push pulses are modulated sinusoidally, which allows applying low frequency mechanical excitation to the tissue. In some embodiments, low frequency waves (<100 Hz) can be generated.

Push and imaging/detection pulses may be interleaved. Only one transducer is needed for both pushing and imaging. In other words, motion excitation and data acquisition can be performed using only one clinical transducer. The transducer may be a linear array transducer. Part or the totality of the elements of the array transducer can be used to generate the shear waves and to image/detect the shear waves.

Imaging pulses may be used to provide 2D data that allows calculating 2D field-of-view (FOV) maps of shear wave speed or shear modulus. The speed map obtained by the present method can be directly compared to those obtained from MRE.

Measurements of speed of the shear wave propagation can be used to provide a full quantitative tissue mechanical properties mapping. The mapping of mechanical properties depends on the capabilities of the transducer. For example, a linear array transducer can provide a 2D map of mechanical properties or a 2D array transducer can provide a 3D mapping of mechanical properties.

According to the embodiments of the present invention, narrowband low frequency excitation and visualization of shear waves are made possible.

BRIEF DESCRIPTION OF THE DRAWINGS

FIG. 5 is a plot showing the periodic change of the push pulses at a constant intensity level;

FIG. 6 is a plot showing the frequency spectrum of the push sequence with the energy concentrating at the main frequency;

FIG. 8A is a 2D FOV shear wave speed map reconstructed using the method of the present invention using the harmonic frequency of 500 Hz on a homogeneous region of a phantom by Computerized Imaging Reference Systems, Inc. (CIRS);

FIG. 8B is a plot showing the time derivative of the phase of the produced shear wave passing through the middle of the region of interest (ROI) corresponding to the shear wave speed map;

DETAILED DESCRIPTION OF THE INVENTION

Overview of the Method

Figure 1:
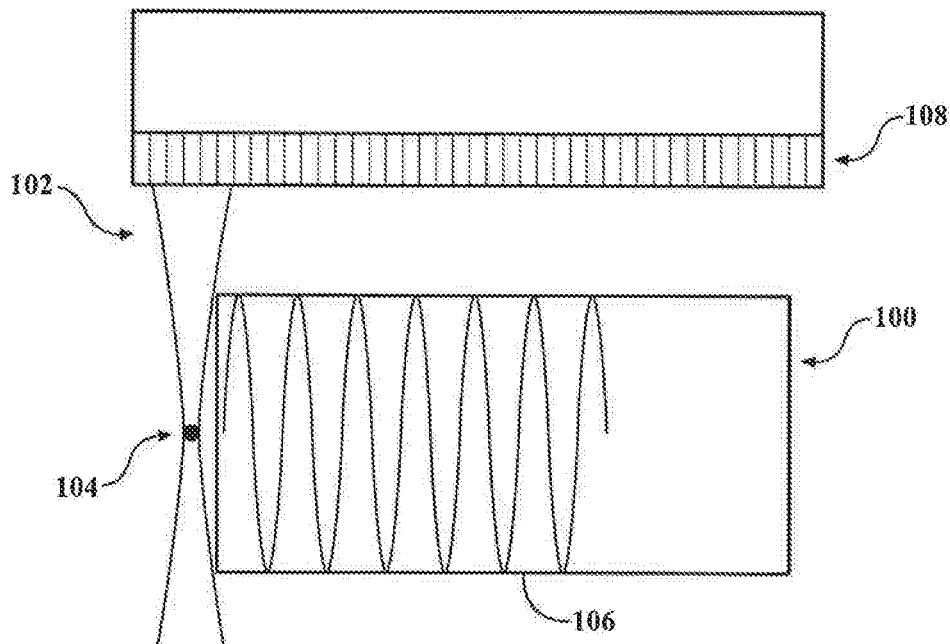
FIG. 1 is a schematic showing a subaperture of elements of a transducer transmitting focused ultrasound push pulses at a chosen focus placed left of a region of interest in accordance with an embodiment of the present invention.

Changes in the stiffness of soft tissues are often related to the presence of pathological conditions. Ultrasound elastography imaging techniques provide noninvasive ways to measure tissue stiffness. In dynamic ultrasound elastography, tissue stiffness is quantitatively evaluated by inducing shear waves in the tissue and monitoring the speed of the shear wave propagation, based on the fact that the shear wave speed is positively proportional to tissue stiffness.

The present invention provides embodiments of a shear wave ultrasound elastography method that allows measurements that may be more robust, and/or more accurate, more consistent.

An embodiment of the present invention provides a shear wave generation method. The shear wave is generated by transmitting periodically-modulated ultrasound "push" pulses with a primary modulation frequency using a transducer. The method, also referred to as harmonic shear wave imaging ((HSWI), successively transmits a series of push pulses to generate an acoustic radiation force that pushes the tissue and induces a shear wave. The push pulses may be periodically modulated either with a periodic change in pulse durations or in pulse magnitudes. In one embodiment, the push pulses are sinusoidally modulated.

In one embodiment, the method uses a single subaperture of elements of a transducer to transmit focused push pulses at a single focal point adjacent a region of interest (ROI). Multiple push pulses are transmitted in a cycle with sinusoidal variation of the acoustic intensity. The cycle will be defined herein below. The change in the acoustic intensity can be achieved by changing the pulse durations, pulse amplitudes, or numbers of active elements in the transducer which are used for transmitting the push pulses.

In one embodiment, the push pulses have different push durations that follow a sinusoidal pattern. A cycle refers to one wavelength of the sinusoidal wave. The shear wave created by a push pulse with a longer duration has a higher amplitude when the acoustic level of the push pulse is fixed. Therefore, the tissue displacement increases proportionally with push duration when the acoustic level of the push pulse is fixed. The sequentially induced shear waves build up together to form a continuous harmonic shear wave with a single frequency equal to the modulation frequency of the acoustic radiation force. The single frequency may be controlled by changing the modulation frequency of the push pulses.

In another embodiment, the push duration is fixed and the intensities of push pulses can be varied to follow a sinusoidal pattern. The periodic changes of the intensities may be caused by the changes of the applied voltages or the aperture size of the elements of the transducer. The displacement produced by each push pulse build up together to form a continuous narrowband shear wave with a single frequency equal to the modulation frequency of the push pulses.

Using the embodiments of the present method, a single transducer may be used for both inducing acoustic radiation force and for imaging. The modulation frequency can be preset and therefore, the frequency of the shear wave can be controlled. In one embodiment, the controlled frequency can be in the range of 50-600 Hz. The lower and upper limits of the frequency can be selected to control the number of wavelengths in the ROI. Controlling the number of wavelengths in the ROI allows improving the accuracy of the calculations of mechanical properties in the ROI.

According to the embodiments of the present invention, a new ultrasound shear wave elastography method capable of generating narrowband shear waves and providing a map of shear wave speed is provided. The speed map may be a 2D field-of-view map. HSWI requires only one clinical transducer that acts both for applying acoustic radiation force excitation and monitoring the tissue response.

In some embodiments, HSWI uses low-frequency, harmonic shear waves with controllable frequencies as a means of evaluating the tissue mechanical properties.

Measurements of speed of the shear wave propagation can be used to provide a full quantitative tissue mechanical properties mapping. The mapping of mechanical properties depends on the capabilities of the transducer. For example, a linear array transducer can provide a 2D map of mechanical properties or a 2D array transducer can provide a 3D mapping of mechanical properties.

HSWI uses several push pulses in a cycle with a sinusoidal variation of pulse duration. The variation in the duration results in a sinusoidal modulation of the acoustic radiation force. Hence, compared to other methods such as shearwave dispersion ultrasound vibrometry (SDUV) that uses only one push pulse per cycle, the intensity and signal to noise ratio (SNR) might be higher in HSWI, which may improve the accuracy of the measurements to evaluate deeper tissues at lower frequencies.

HSWI can use plane wave pulses to measure 2D maps of shear wave speed. HSWI generates shear waves with a narrowband main frequency to perform the measurement. The measurement can be repeated several times at different main frequencies for evaluating the viscoelastic properties of tissue by analyzing dispersion. Because shear waves at high frequency are typically weak and quickly attenuated, HSWI can operate to frequencies approximately up to 550 Hz. Thus, HSWI is a useful measurement technique in a wide frequency range.

It is difficult to control the amplitude (or energy) of the wave at specific frequencies in transient methods. Unlike transient methods, the energy in HSWI is concentrated around a narrow frequency range controlled by the user. The frequency spectrum of the push pulse sequence shows that HSWI concentrates most of the energy at the main frequency that is comparable to MRE, which typically operates at a single frequency between 50-100 Hz. Hence, it is reasonable to expect that shear waves with higher intensity are generated in HSWI, especially at lower frequencies. Shear waves with higher intensity allow probing the tissue at different frequencies, and are likely to result in better SNR and more accurate SWE results.

Local frequency estimation (LFE), the inverse method selected in one embodiment of the present invention for reconstructing the 2D map of shear wave speed, has intrinsic limitations related to the wavelength and ROI size. A more accurate estimation of shear wave speed is obtained when a higher number of cycles of harmonic shear waves is present within the ROI. The wavelength is longer if a lower harmonic frequency is being used or a stiffer material is being measured, and therefore a larger ROI is needed to cover more wavelengths. The use of higher harmonic frequency may mitigate this problem. The use of curvilinear transducers may also be able to mitigate this issue, since they operate with an extended field of view. The attenuation per unit distance is proportional to the frequency, so higher-frequency shear waves may not be able to propagate a long distance through the width of the ROI. In some embodiments, other inverse methods for reconstructing the 2D map of shear wave speed can be adopted.

The amplitude of the motion at the focal point can be easily measured from the wave pattern generated by HSWI. The measurements can be repeated for different focal points, generating a map of the tissue motion amplitude.

A characteristic of HSWI is that shear waves are generated by sinusoidal variation of the acoustic radiation force. Therefore, the generated shear wave and its wave speed are less dependent on tissue properties, such as absorption, and other characteristics of the ultrasound system such as frequency and transducer type. Therefore, the measured shear wave speed measured by HSWI can potentially be independent of the device and transducer being used.

A mathematical viscoelastic model may be used to fit the functional relationship between the shear wave speed and harmonic frequency to calculate the viscoelastic properties, including the elasticity and viscosity, of the tissue.

The ability of HSWI for detecting inclusion of different stiffness may be analyzed. To do this, an optimization of HSWI and LFE parameters (or another inverse method) is required in order to accurately quantify and detect small inclusions. However, application such as liver fibrosis staging and tendon mechanics may not require the ability of identifying inclusions with sizes in the millimeter range. Consequently, using LFE and current HSWI parameters may work for those applications. Other inverse methods may be considered for clinical conditions requiring higher spatial resolution.

Examples of HSWI

Figure 2:
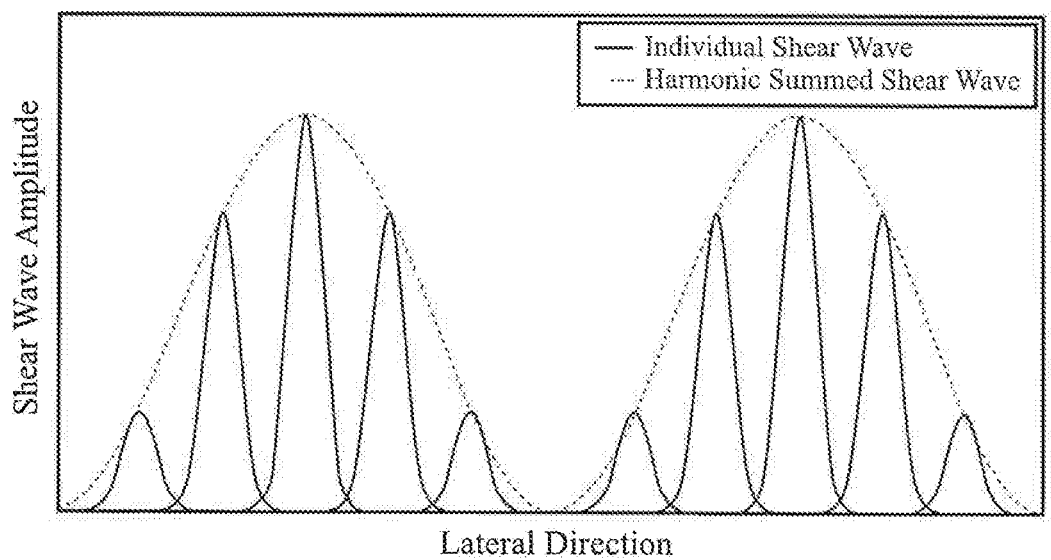
FIG. 2 is a plot showing sequentially induced shear waves with a sinusoidal variation of amplitude that are built up together to form a continuous narrowband shear wave.

In one embodiment, a Verasonics ultrasound system (Verasonics Inc., Redmond, WA) with a linear array transducer L7-4 (128 elements, beamwidth=4-7 MHz, center frequency=5.208 MHz) is used to implement the HSWI method in the present invention. In HSWI, the transducer's sub-aperture of 32 elements 108 successively transmits a series of focused ultrasound beams (push pulses) 102 at a chosen focus 104 placed left of the region of interest (ROI) 100, as shown in FIG. 1. The intensity of each push pulse is varied in a sinusoidal pattern. Several parameters can be used to modulate the intensity of each push pulse, such as the magnitude of the applied voltage, the duration of the pulse, and the aperture size. In this embodiment of HSWI, the intensity of the push pulse is modulated by controlling the pulse duration. The induced shear waves are built up together to form a continuous harmonic shear wave with a main harmonic frequency equal to the frequency at which the pulse duration is varied, as shown in FIG. 2. In one embodiment, the pulse duration is set to change sinusoidally between $D_{min}$=9.6 µs (50 cycles at 5.208 MHz) and $D_{max}$=105.6 µs (550 cycles at 5.208 MHz). The harmonic frequency at which pulse duration is varied is denoted by $f_s$ and can be controlled by the user in the range of 50 to 600 Hz. The duration of the $n^{th}$ push pulse may be set by the following equation:

$$D_n = D_{min} + \frac{(D_{max} - D_{min})}{2}[\sin(2\pi(n-1)/N_{pp}) + 1] \quad (1)$$

where n={1, 2, . . . , $N_{pp}$}. One complete excitation cycle is constructed by a preset number of push pulses ($N_{pp}$). The $N_{pp}$ at each frequency is chosen to produce smooth sinusoidal waves. To cover the entire ROI and avoid transient effects, multiple cycles ($N_{cycle}$) of push pulses may be transmitted. The excitation parameters are summarized in Table 1. There is a timing limitation to the number of push pulses per cycle that can be applied at a given frequency. But, there is no need to use the maximum number of push pulses possible to obtain smooth waves. For example, using 4 push pulses per cycle may be enough to produce smooth sinusoidal shear waves for frequencies higher than 200 Hz. Using a low number of pulses may be desirable in terms of acoustic safety to reduce the amount of energy delivered to the tissue. For lower frequencies, more pulses may be needed to produce smooth waves.

TABLE I

Parameters used in the generation of harmonic
shear waves at different frequencies

| | Harmonic frequency (Hz) | | | | | | | |
|---|---|---|---|---|---|---|---|---|
| | 100 | 200 | 250 | 400 | 450 | 500 | 550 | 600 |
| $N_{pp}$ | 10 | 4 | 4 | 4 | 4 | 4 | 4 | 4 |
| $N_{cycles}$ | 2 | 3 | 3 | 5 | 5 | 6 | 6 | 6 |
| $N_{angles}$ | 3 | 3 | 3 | 2 | 2 | 2 | 2 | 2 |

Figure 3:
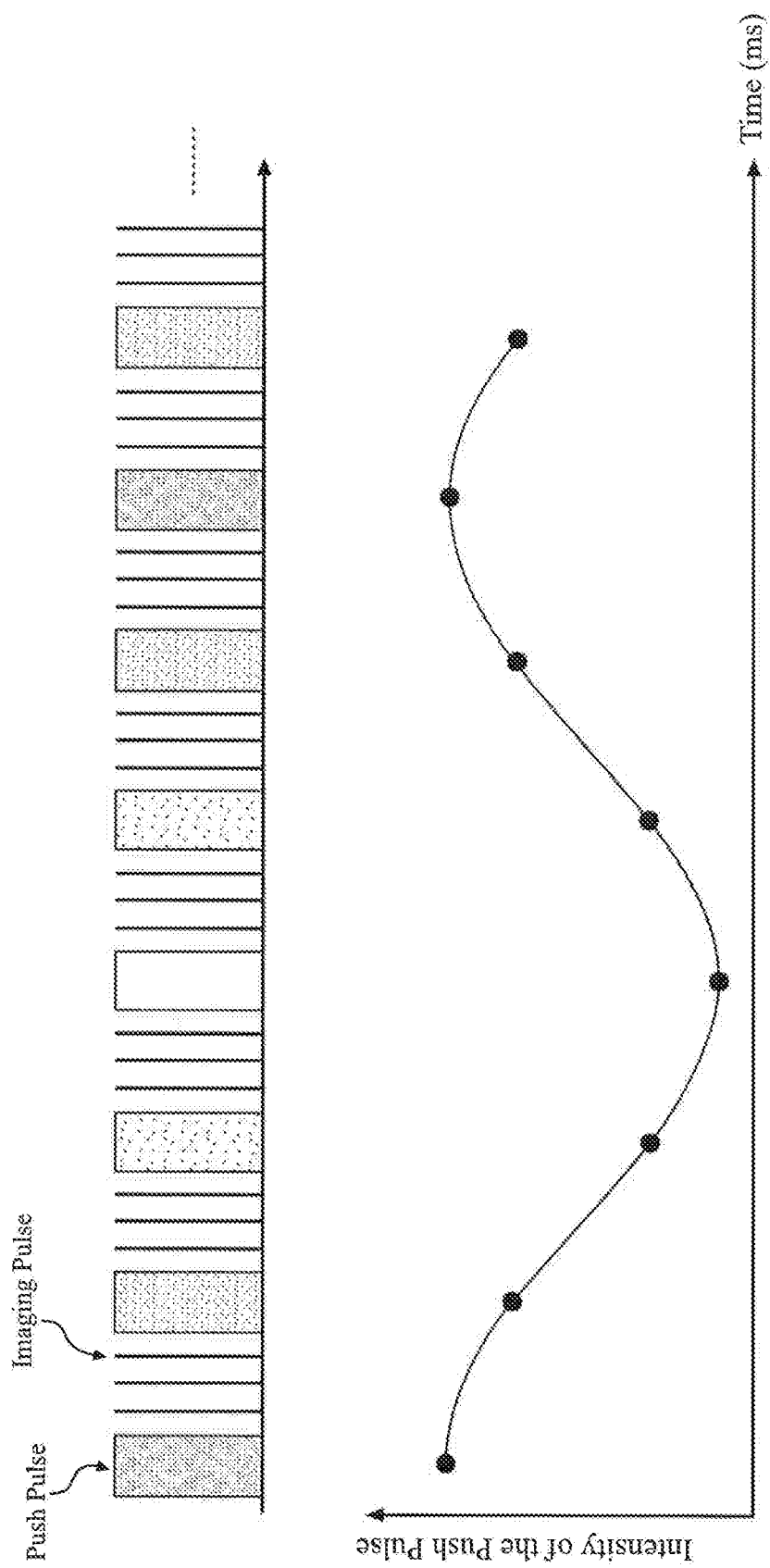
FIG. 3 is a schematic (top) and a plot (bottom) showing that interleaving imaging pulses and push pulses are provided and the intensity of the push pulses is sinusoidally modulated at a controllable harmonic frequency.
Figure 4:
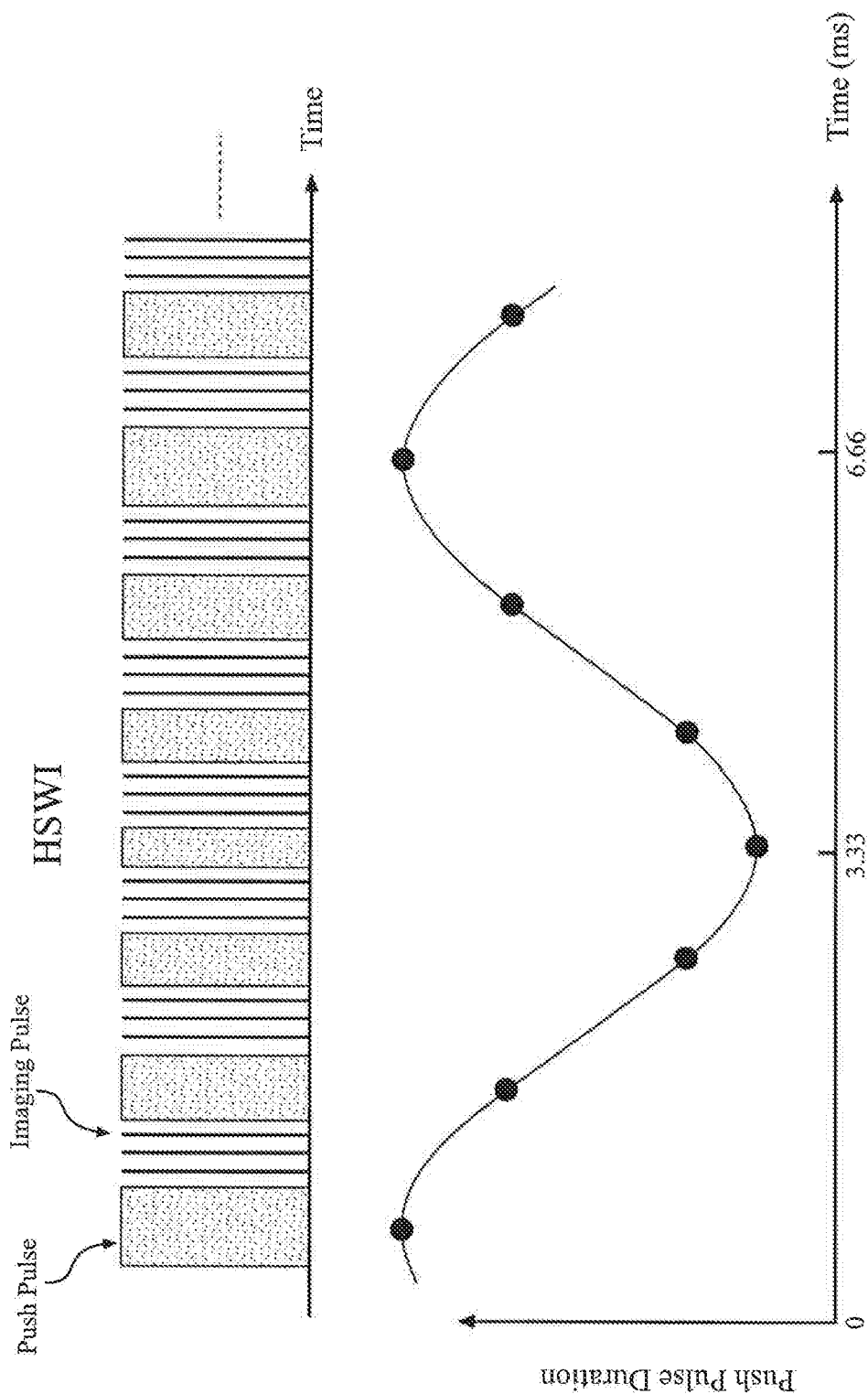
FIG. 4 is a schematic (top) and a plot (bottom) showing that interleaving imaging pulses and push pulses are provided and the duration of the push pulses is sinusoidally modulated at controllable harmonic frequency (the width of the push pulse represents the amplitude of the duration of the push pulse)

Between each push pulse, plane wave imaging pulses may be transmitted to track the shear wave propagation, as shown in FIG. 3 top part. The imaging rate is a multiple of the shear wave frequency. The schematic push pulses and imaging sequences for these two methods are shown in FIGS. 3-5. HSWI uses multiple push pulses per cycle with varying duration. As shown in FIG. 3, HSWI measures shear waves propagating in the field of view by interleaving imaging pulses and push pulses. The intensity of the push pulses is sinusoidally modulated at a controllable harmonic frequency, as indicated in FIG. 3 bottom part. The grey scale level of the push pulse represents the amplitude of the intensity of the push pulse.

FIG. 4 also shows HSWI push pulses and imaging sequences. The schematic six push pulses at the main frequency of 150 Hz are shown interleaving with imaging pulses. The duration of the push pulses is sinusoidally modulated at a controllable main frequency. The duration of the push pulse is represented by the width of the push pulse. FIG. 5 shows an example of change in pulse duration and shear wave intensity of push pulses in the HSWI at the main frequency of 150 Hz.

Several tilt angles may be used to obtain one averaged image frame in an attempt to improve the signal-to-noise ratio of the image. In this example, three- or two-angle compounding plane wave pulses may be used in the lower (250 Hz or lower) and higher (400 Hz or higher) harmonic frequency mode, respectively, as shown in Table I. Fewer compounding plane wave pulses may be used at higher frequencies due to timing constraints. Alternatively, coded excitation may be used to send several plane waves simultaneously. This may be beneficial, especially in the high frequency range, and can help solve the timing constraint. Particle displacements are estimated by calculating the phase difference between consecutive frames.

Compounding plane wave pulses with three angles (−15°, 0° and 15°) were used to improve the SNR and lateral resolution of acquisition pulses. However, due to timing constrains, for frequencies higher than 250 Hz only two angles were used, as indicated in Table 1. The acquisition of the different plane-wave angles was done in between consecutive push pulses and compounded into a single frame. Therefore, the imaging rate was not changed as a function of the number of angles. The image acquisition started after $N_{Cycles}$ push cycles were fired to ensure the transient effects were not present.

Fourier transform is performed on the phase data in the time coordinate, and the component corresponding to the excitation harmonic frequency ($f_s$) is kept. A spatial low-pass filter and a directional filter may be used to remove noise and select shear waves propagating away from the focal point (i.e., filtering waves reflected from the walls of the phantom containers).

Fourier analysis of the sequence of push pulses used in HSWI indicated that the majority of the excitation energy concentrates at the main frequency. The HSWI frequency spectrum is shown in FIG. 6. The intensity in HSWI was normalized by dividing by the intensity obtained for SDUV at the main frequency.

2D Mapping of the Shear Wave Speed

The time derivative of the phase was estimated by calculating the phase difference between consecutive frames. Fourier transform is applied to the time derivative of the phase data and the component at the excitation frequency was kept. A directional filter was used to filter waves reflected from the walls of the phantom containers.

Figure 7A:
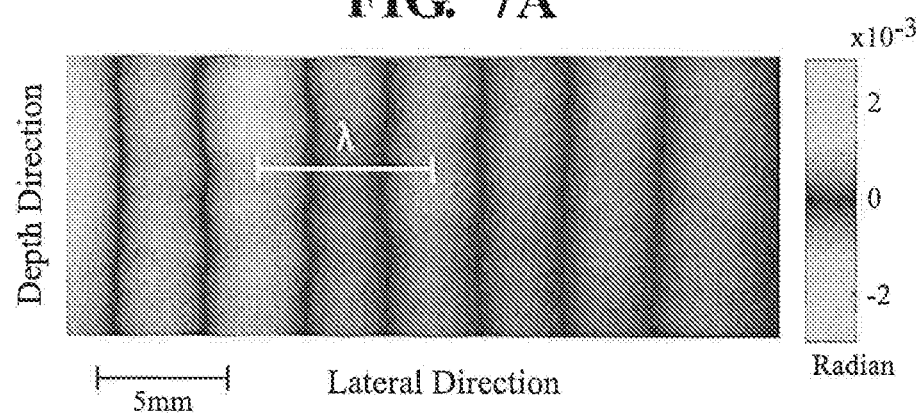
FIG. 7A is an image showing an example of a shear wave pattern.
Figure 7B:
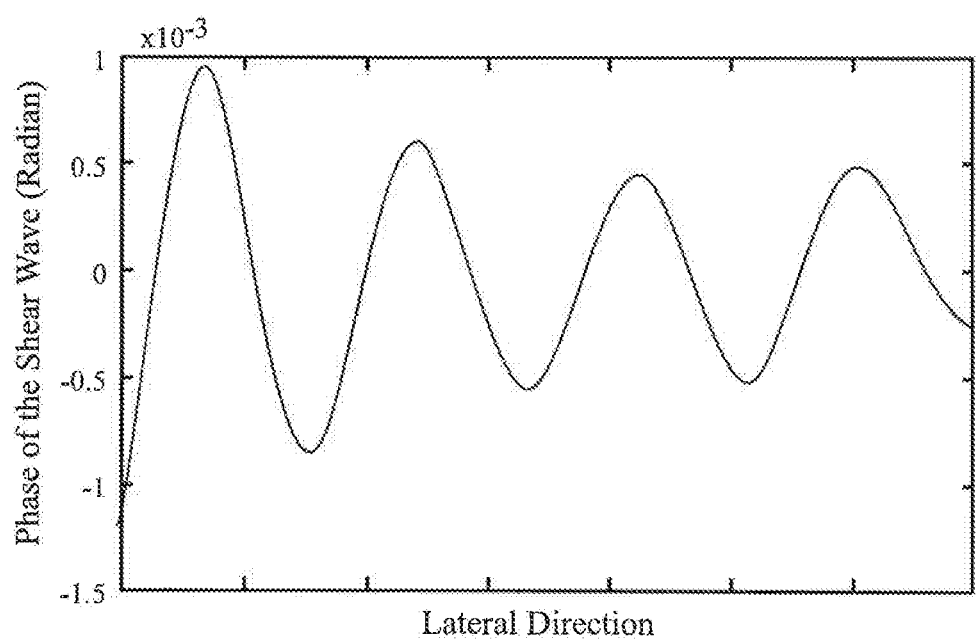
FIG. 7B is a plot showing the signal through the field-of-view (FOV) at the focal depth (indicated by the arrow in FIG. 7A) of the acoustic radiation force excitation.

A representative map of the harmonic shear wave propagation is shown in FIG. 7A. FIG. 7B shows the amplitude of the generated harmonic shear wave at the focal depth, indicated by the arrow in FIG. 7A. As shown in FIG. 7B, the decay in the amplitude of the shear wave as a function of distance from the focal point can be measured. This measurement may be useful for the calculation of additional mechanical properties of the tissue.

The filtered IQ data can be post-processed to obtain a 2D image showing the pattern of the harmonic shear wave propagation though the tested material. The wavelength ($\lambda$) of the harmonic shear wave can be identified and measured from the wave pattern.

The filtered phase data may be processed using Local Frequency Estimation (LFE) to obtain the 2D quantitative map of shear wave speed. LFE calculates the shear wave speed by estimating the local spatial frequency of the shear wave propagation pattern through an algorithm which combines local estimates of instantaneous frequency over several scales.

The estimation is calculated by a bank of spatially oriented lognormal quadrature filters. In one embodiment, a bank of 8 quadrature filters is used, which are a product of radial and directional components. Combining the outputs from two sets of filters which differ only in center frequency produces a local frequency estimate. LFE allows material parameters to be estimated without explicitly invoking the coupled or uncoupled equations of motion and eliminates the need to numerically compute second or higher order spatial derivatives. However, estimates of mechanical properties based on LFE can be corrupted by rigid body motion and dilatational waves in displacement data. The lower value of shear wave speed at the edges of the field of view are caused by inaccuracies of the LFE method.

One limitation of LFE is that accurate calculations can be obtained only if the ROI contains at least half of a wavelength of the harmonic shear wave. Hence, in the present method, the rationale for determining the size of the ROI is to assure that two to three complete cycles of harmonic shear waves are present within the ROI. In stiff materials with long wavelengths, the ROI size may be set to its maximal value of 320 mm, which is determined by the transducer size. For those cases, the accuracy of LFE could not be guaranteed. Therefore, a 1D estimation of the shear wave speed based on manual measurements of wavelength is also performed.

1D Estimation of the Shear Wave Speed

The wavelength of the harmonic shear wave can be identified by observing the 2D wave pattern, as shown in FIG. 7A. If the tested material is homogeneous, the wavelength of the harmonic shear wave should be constant throughout the field-of-view (FOV). By estimating the wavelength ($\lambda$) of the harmonic shear wave on the image, as shown in FIG. 4A at a specific harmonic frequency ($f_s$) the shear wave speed ($v_s$) of the tested material can be calculated by the relationship:

$$v_s = \lambda f_s \quad (2)$$

This calculated shear wave speed is defined as the 1D estimate of shear wave speed, and is considered to be close to the theoretical shear wave speed of the material. In one embodiment of the present invention, for each homogeneous phantom, the 1D shear wave speed is calculated and compared to the shear wave speed estimated by LFE. Preliminary investigation found that the phantoms tested in this study showed no significant dispersion effect. Therefore, the measured shear wave speeds are independent of the applied harmonic frequency. In the present method, the 1D shear wave speeds of the phantoms at the harmonic frequency of 500 Hz are reported.

Phantom Measurements and Ex Vivo Experiments

The ability of HSWI to accurately measure the shear wave speed and to differentiate tissues of different stiffness was investigated on a calibrated homogeneous elasticity phantom (nominal shear wave speed=2.94 m/s, Model 040GSE, Computerized Imaging Reference Systems, Inc. (CIRS), Norfolk, Virginia, USA), as well as a series of agarose gels with different concentrations (0.4, 0.5, 0.6, 0.7, 0.8, and 0.9 w/w). Each agarose gel may be mixed with a constant concentration of $MgCO_3$ (0.5% w/w) that is used to produce ultrasound scatters. Each phantom was measured by HSWI with the harmonic frequencies of 100, 200, 250, 400, 450, 500, 550 and 600 Hz. For comparison and validation of HSWI, the CIRS phantom was measured by a custom implementation of SSI, and the agarose gels were measured by both SSI and MRE. The harmonic frequency used in the MRE measurement was 500 Hz (same as in the 1D estimation). The agarose gels for the MRE measurement were not mixed with $MgCO_3$ to avoid artifacts in the images.

Ex vivo experiments were conducted on the tibialis cranialis muscle of a swine leg and a swine liver tissue for testing the feasibility of HSWI to measure the mechanical properties in real tissues at harmonic frequencies of 400, 450, 500, 550 and 600 Hz. The tissues were tested immediately after they are acquired from the local butcher shop, and kept at room temperature during testing. The tissues were also measured using SSI.

The accuracy of the results in a CIRS phantom were determined by comparing the obtained shear wave speed values with the nominal value provided in the phantom data sheet. The measurement depth was 1.5 cm. The ROI size used in each case is presented in Table 2. The ROI height was constant (1 cm) in all cases. The maximum ROI width that could be used in this study was 3.3 cm, which was constrained by the size of the transducer.

TABLE II

THE ROI WIDTH (IN CM) USED AT DIFFERENT FREQUENCIES IN DIFFERENT PHANTOMS AND MUSCLE

| | HSWI | | | | | |
|---|---|---|---|---|---|---|
| | 100 Hz | 200 Hz | 250 Hz | 450 Hz | 500 Hz | 550 Hz |
| Rectus femoris muscle | 3.3 | 3.3 | | | 2.4 | |
| CIRS | 3.3 | 3.3 | | | 2.4 | |
| 0.4% agarose | 3.3 | 2.7 | | | 0.9 | |
| 0.5% agarose | 3.3 | 2.7 | | | 1.2 | |
| 0.6% agarose | 3.3 | 3.3 | | | 1.95 | |
| 0.7% agarose | 3.3 | 3.3 | | | 1.95 | |
| 0.8% agarose | 3.3 | 3.3 | | | 2.4 | |
| 0.9% agarose | 3.3 | 3.3 | | | 2.85 | |

Preliminary results indicate that the ROI width for the lower frequency (100, 200 and 250 Hz) should be larger than that for the higher frequency (450, 500 and 550 Hz). The reason for this was that LFE accurately estimated the shear wave speed only if two or more wavelengths were included in the ROI. However, the same size of ROI used at lower frequencies could not be used at higher frequencies since attenuation produced an area inside the ROI with low amplitude shear waves that caused LFE to produce inaccurate estimations of wave speed. Hence, a smaller ROI (but large enough to include at least two wavelengths and ensure successful shear wave propagation inside the ROI) was used for higher frequencies. For each case, the mean shear wave speed was calculated from the speed map and used as representative value for the sample. Measurements were repeated five times. The mean and standard deviation values of the five trails were reported at each case.

For comparison, a custom implementation of the supersonic imaging (SSI) method for elastography was implemented in the Verasonics system using a L7-4 linear array transducer and an applied voltage of ±40 V. For SSI, an aperture of 64 transducer elements emitted focused push pulses (500 cycles at 5.208 MHz) successively at seven, equally spaced focal depths, creating quasi-plane shear waves. The propagation of the quasi-plane shear wave was measured using plane wave imaging at 10,000 frames/s. The time derivative of the phase was estimated in the same way as in HSWI. The shear wave speed was calculated by cross-correlation of the time variation of the time derivative of the phase in two points separated by 1.0 mm. The ROI size was 1 cm×1 cm. The measurement depth was 1.5 cm, the same as that in the HSWI measurements. For each case, the measurement was repeated five times, and the mean and standard deviation values were calculated. Additionally, to compare the results of HSWI and SSI at each frequency, the dispersion curve was obtained by applying 2D fast Fourier transform (FFT) on the displacement data obtained in the CIRS phantom using SSI to obtain frequency-dependent shear wave speed.

A 3T magnetic resonance imaging scanner (Siemens MAGNETOM Prisma fit, Erlangen, Germany) with a MRE technique as previously described was also used to measure the shear modulus of agarose gels. MRE measurements were performed in agarose phantoms that were small (about 4 cm×4 cm). In order to have several wavelengths inside the phantoms, higher frequencies had to be used. The frequency used in the MRE measurement was 500 Hz. The agarose gels for the MRE measurement were not mixed with $MgCO_3$ to avoid artifacts in the images. The measurement was performed in one agarose sample (n=1) per concentration.

In Vivo Measurements

HSWI was also performed in the rectus femoris muscle of a healthy male individual to evaluate the HSWI performance in vivo. The participant laid supine on the table with the calves and the knees hanging off the table. Since SWE results are sensitive to the degree of muscle contraction and transducer position, it is crucial to control these parameters to produce reliable and precise results. Ultrasound SWE has been found to be a reliable method when the transducer is placed parallel to the muscle fiber orientation. Therefore, elastography measurement was performed by placing the ultrasound transducer in a longitudinal view along the length of the muscle fibers until a clear image of the fibers inside muscle could be identified. The measurement depth (from the transducer surface to the bottom of the ROI) was 3 cm. It was also measured by a custom implementation of SSI in the Verasonics system using a L7-4 linear array transducer and an applied voltage of ±40 V.

Measurement of the Acoustic Output Parameters

In order to use HSWI for clinical imaging, it is necessary to verify that the acoustic output parameters do not exceed the limits set by the FDA. The acoustic output parameters are measured using a hydrophone (HGL-0200, ONDA Corporation, Sunnyvale, CA, USA). During the measurement, the focal depth of the push pulses is adjusted from 5 mm to 10 mm with a step size of 1 mm, and then from 10 to 40 mm with a step size of 5 mm. The hydrophone is mounted on a mechanical positioning system with a displacement resolution of 0.1 mm. The output voltage from the hydrophone is recorded using a digital oscilloscope (Tektronix MD03012, Beaverton, OR, USA), and sent to a laptop computer for processing. Three derated acoustic output parameters, the spatial-peak temporal-average intensity ($I_{SPTA,0.3}$), the spatial-peak pulse-average intensity ($I_{SPPA,0.3}$) and the mechanical index (MI) are measured. The FDA sets the limits for musculoskeletal applications for these parameters as: $I_{SPTA,0.3}$<720 mW/cm$^2$, $I_{SPPA,0.3}$<190 W/cm$^2$ or MI<1.9. $I_{SPTA,0.3}$ and $I_{SPPA,0.3}$ are calculated by $$I_{SPTA,0.3} = PII_{0.3} \cdot PRF \quad (3)$$

$$I_{SPPA,0.3} = PII_{0.3}/PD \quad (4)$$

where PRF is the pulse repetition frequency (Hz) and is set as ⅓ Hz in one embodiment of the present method. PD is the pulse duration (sec), and its value depends on the number of cycles of push pulses ($N_{cycles}$) and the harmonic frequency used. $PII_{0.3}$ is the pulse intensity integral derated at a rate of 0.3 dB/cm/MHz, and is calculated by $$PII_{0.3} = PII \cdot e^{-0.23 \cdot 0.3 \cdot f_c \cdot z} \quad (5)$$

where $f_c$ is the center frequency of the transducer (MHz), and z is the distance (cm) along the beam axis from the transducer to the focus. PII is calculated by $$PII = \frac{\int_{t_1}^{t_2} v_h^2(t) dt}{10^4 \rho c M_L^2(f_c)} \quad (6)$$

where $\rho$ is the medium density (kg/m$^3$), c is the sound speed in the medium (m/s), $M_L(f_c)$ is the hydrophone sensitivity (V/Pa) at $f_c$, and $v_h(t)$ is the voltage data measured by the hydrophone. The integration is performed over the time interval $t_1$ to $t_2$ in which the voltage data for a specific pulse is non-zero.

MI is calculated by $$MI = |p_{r,0.3}|/\sqrt{f_0} \quad (7)$$

where $p_{r,0.3}$ is the peak rarefactional pressure derated at a rate of 0.3 dB/cm/MHz, and is calculated by $$p_{r,0.3} = p_r \cdot e^{-0.115 \cdot 0.3 \cdot f_c \cdot z} \quad (8)$$

where $p_r$ is calculated from the hydrophone output voltage data as $\min[v_h(t)]/M_L(f_c)/10^6$.

Results

Table III shows the shear wave speeds of the CIRS phantom and agarose gels measured by HSWI (using LFE and 1D estimation), MRE and SSI. In general, a good agreement between the shear wave speeds measured by HSWI using LFE and 1D estimation can be observed, demonstrating that LFE can potentially be used as an inverse method for HSWI. However, in some cases (marked by asterisks in Table II), LFE failed to provide an accurate estimate. In those cases, the estimation of shear wave speed is significantly lower. In this embodiment, the 1D estimation of shear wave speed is comparable to those by MRE, and the difference between the two methods is 0.7 to 4.6%. Compared to SSI, the HSWI and MRE measurements are lower (differences of 1.0 to 19.3% were observed). FIG. 8A shows a 2D FOV shear wave speed map reconstructed by HSWI using the harmonic frequency of 500 Hz on the CIRS phantom as an example. FIG. 8B shows the amplitude of the corresponded shear wave signal passing through the middle of the ROI.

Figure 10:
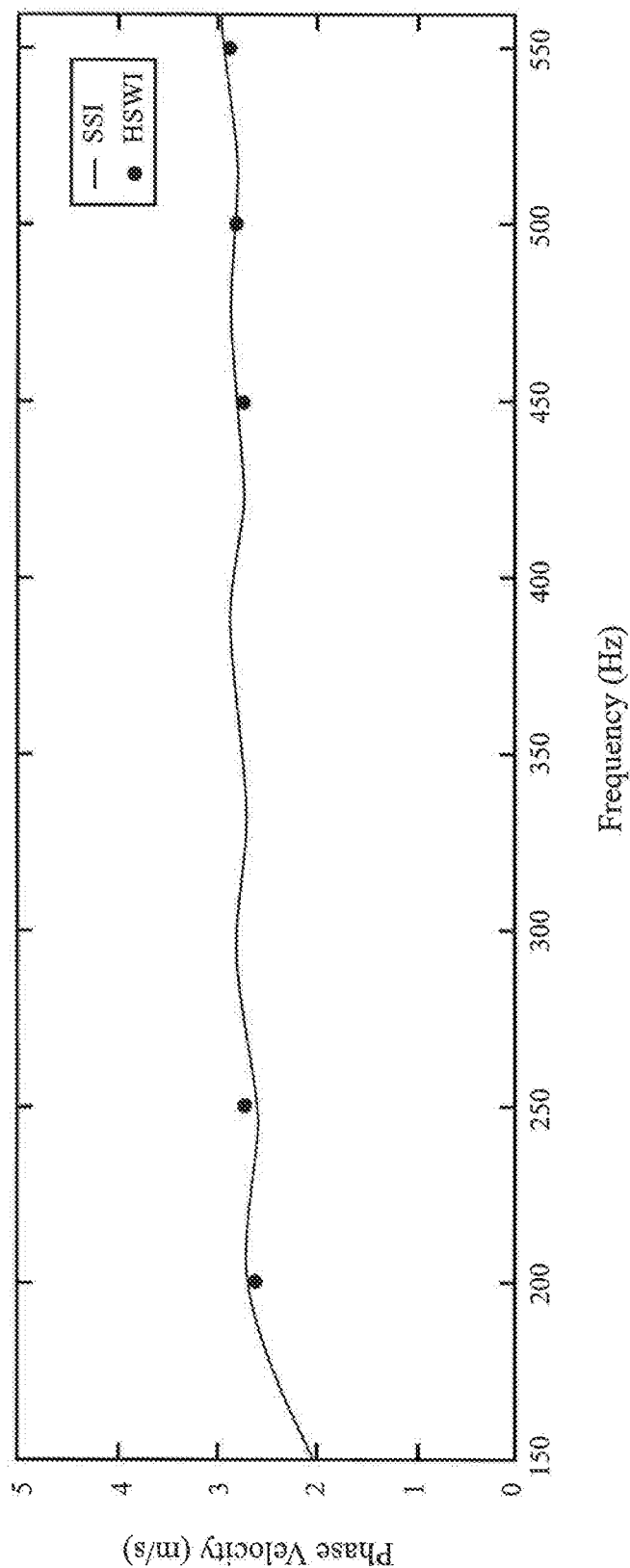
FIG. 10 is a plot showing a comparison between the shear wave phase velocities of the CIRS phantoms obtained by the SSI and HSWI methods.

Additionally, the comparison between the dispersion curve obtained in the CIRS phantom using SSI and shear wave speed obtained using HSWI are shown in FIG. 10.

TABLE III

Shear wave speeds of the CIRS phantom and agarose gels with different concentrations of agarose

| Phantom | HSWI | | | | | | | | 1D | MRE | SSI |
| --- | --- | --- | --- | --- | --- | --- | --- | --- | --- | --- | --- |
| | 100 Hz | 200 Hz | 250 Hz | 400 Hz | 450 Hz | 500 Hz | 550 Hz | 600 Hz | | | |
| CIRS | 2.70 | 2.79 | 2.86 | 2.93 | 2.89 | 2.89 | 2.99 | 3.03 | 2.96 | N/P | 2.99 |
| 0.4% | 1.37 | 1.53 | 1.54 | 1.55 | 1.57 | 1.52 | 1.57 | 1.53 | 1.50 | 1.57 | 1.64 |
| 0.5% | 1.69* | 1.97 | 1.95 | 1.91 | 1.94 | 1.87 | 1.96 | 1.94 | 1.91 | 1.96 | 2.28 |
| 0.6% | 2.04* | 2.63* | 2.53* | 2.96 | 3.05 | 2.98 | 2.94 | 3.01 | 2.99 | 2.94 | 2.93 |
| 0.7% | 2.11* | 2.75* | 2.93 | 3.13 | 3.17 | 3.09 | 3.19 | 3.21 | 3.15 | 3.13 | 3.38 |
| 0.8% | 1.84* | 2.89* | 3.16* | 3.77 | 3.82 | 3.72 | 3.70 | 3.80 | 3.77 | 3.72 | 3.98 |
| 0.9% | 1.47* | 3.59 | 3.42* | 3.98 | 3.92 | 3.87 | 4.09 | 4.02 | 3.94 | 3.91 | 4.22 |
| 1.0% | 1.88* | 2.94* | 3.87* | 3.83* | 4.41 | 4.44 | 4.41 | 4.39 | 4.37 | 4.30 | 4.66 |

Figure 9A:
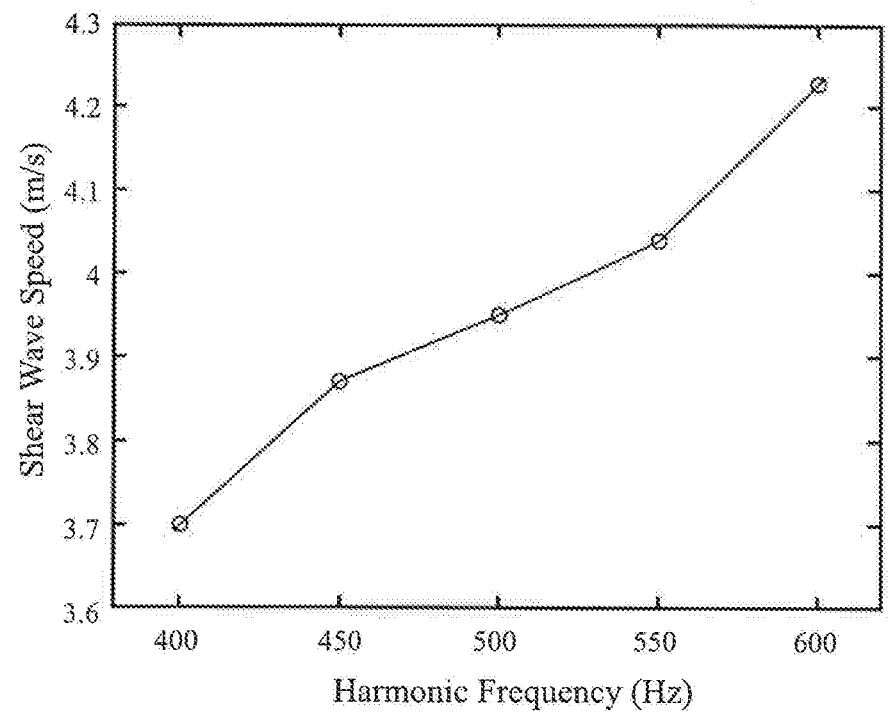
FIG. 9A is a plot showing the shear wave speed as a function of the harmonic frequency on a swine tibialis cranialis muscle measured by the method of the present invention.
Figure 9B:
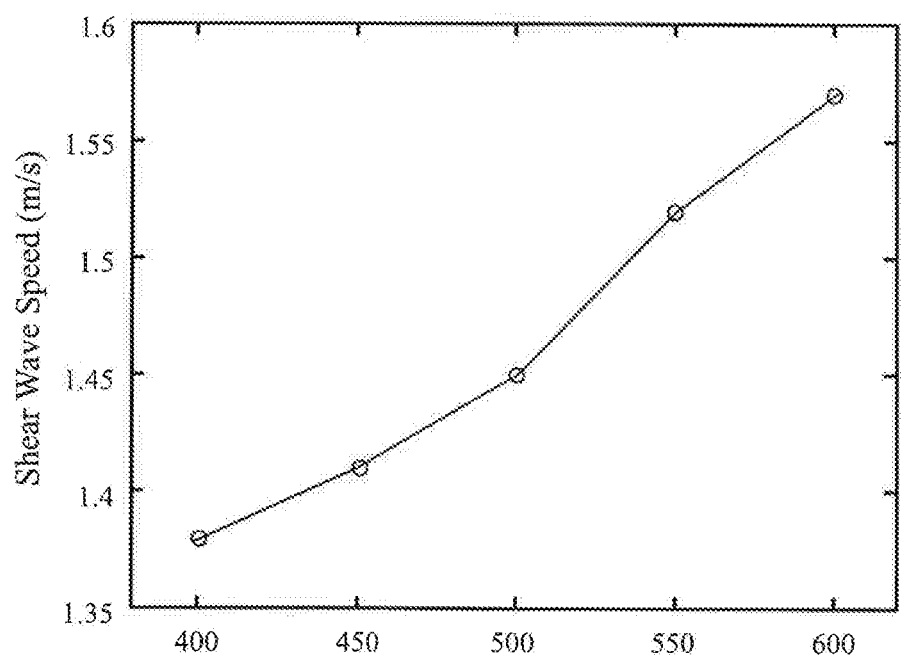
FIG. 9B is a plot showing the shear wave speed as a function of the harmonic frequency on swine liver tissue.

The shear wave speed as a function of the harmonic frequency on the swine tibialis cranialis muscle and the swine liver tissue in the ex vivo experiments is shown in FIGS. 9A and 9B. It can be observed that the measured shear wave speed increased with the harmonic frequency, demonstrating the dispersion characteristics of biological tissues. The shear wave speed measured by SSI on the swine tibialis cranialis muscle and the swine liver tissue is 3.89 and 1.79 m/s, respectively.

In the measurement of the acoustic output parameters, it is found that the maximum values of $I_{SPTA,0.3}$, $I_{SPPA,0.3}$ and MI occurred 5 to 8 mm from the transducer surface. Each of the three parameters is found to decrease with increasing depth below where the maximum value occurred. The maximum values of $I_{SPTA,0.3}$, $I_{SPPA,0.3}$ and MI for each harmonic frequency are reported in Table IV. It can be observed that the harmonic frequencies of 500, 550 and 600 Hz have similar $I_{SPTA,0.3}$. This is because these three harmonic frequencies applied the same number of $N_{cycles}$ and $N_{pp}$, and $I_{SPTA,0.3}$ is dependent on $N_{cycles}$ and $N_{pp}$ but is independent of the harmonic frequency used. The same is true for the harmonic frequencies of 400 and 450 Hz, as well as for 200 and 250 Hz. For $I_{SPPA,0.3}$, each harmonic frequency had different values, because $I_{SPPA,0.3}$ is dependent on PD that is related to the harmonic frequency used. Since MI is a function of the minimum of the output voltage and that is the same for every harmonic frequency, the values of MI are similar for every harmonic frequency. For each harmonic frequency, the maximum $I_{SPTA,0.3}$ is lower than the FDA limit (720 mW/cm$^2$). Hence, although the maximum MI did not meet the requirement (<1.9), it is acceptable because the maximum $I_{SPPA,0.3}$ is below the limit (190 W/cm$^2$).

HSWI is a method that measures maps of harmonic shear waves. The results in the present invention showed that the shear wave speeds of the agarose gels measured by HSWI and MRE were very similar.

The measurement of the acoustic output parameters showed that acoustic intensities are below the current FDA regulatory limits for clinical musculoskeletal applications. These features make HSWI a good candidate to be implemented on commercial ultrasound scanners and used in clinical practice.

The shear wave speeds of the phantoms measured by HSWI and SSI were similar. The phase velocity as a function of frequency was measured using SSI with Fourier post-processing and HSWI at different discrete frequencies. The change in phase velocity had almost flat distribution in the range of 200-550 Hz, with the good agreement between the two methods. The gel phantoms measured were not dispersive and the shear wave speeds should be independent of frequency. Hence, the two methods should produce similar measurement results. It should also be noticed that since the biological tissues are viscoelastic, the measured shear wave speeds by HSWI and SSI may be significantly different for biological tissues due to the difference in the bandwidth of the excitation pulses between the two methods. This can be observed in the measurements performed in the rectus femoris muscle (Table III), where the speed measured using HSWI ranged from 2.11 to 3.06 m/s, while the speed measured using SSI was around 2.56 m/s.

The embodiments of the present invention introduce a narrowband shear wave generation and shear wave detection technique using a single clinical transducer. HSWI may produce similar results to MRE due to the harmonic nature of the mechanical excitation.

TABLE IV

Maximum values of acoustic output parameters ($I_{SPTA,0.3}$, $I_{SPPA,0.3}$ and MI) for each harmonic frequency

| Parameters | 100 Hz | 200 Hz | 250 Hz | 400 Hz | 450 Hz | 500 Hz | 550 Hz | 600 Hz |
|---|---|---|---|---|---|---|---|---|
| $I_{SPTA,0.3}$ | 406 | 309 | | 515 | | | 618 | |
| $I_{SPPA,0.3}$ | 61 | 62 | 77 | 124 | 138 | 154 | 170 | 185 |
| MI | | | | <2.5 | | | | |

CONCLUSION

In principle, the measurement results of shear wave speed by HSWI are comparable to MRE and other harmonic methods such as Tissue Harmonic Imaging (THI), due to the temporal characteristic of the wave excitation. Producing similar results to MRE is important because MRE is a well-established clinical method with high accuracy, sensitivity and specificity, and is useful for clinical applications such as staging of liver fibrosis.

Frequency domain analysis showed that most of the ultrasound energy concentrates at the main frequency. Phantom experiments showed that the shear wave speeds obtained using HSWI and MRE were comparable. The results from HSWI in the rectus femoris muscle of a healthy male individual showed an increase of speed with frequency, as expected, due to the viscoelasticity of the tissue. The values measured with SSI were close to those obtained by HSWI at 200 Hz. It can be seen that for lower frequencies, similar to those commonly used in MRE, the wave speed measured by HSWI is lower. Therefore, this represents an example of the difference between HSWI and SSI in vivo.

The results of the ex vivo experiments showed that the measured shear wave speed increased with the harmonic frequency, demonstrating the capability of HSWI to assess the dispersion characteristics of real tissues. For the swine tibialis cranialis muscle, shear wave speed values were between 3.70 and 4.23 m/s for harmonic frequencies between 400 and 600 Hz. For the swine liver tissue, shear wave speed values ranged from 1.38 and 1.57 m/s for harmonic frequencies between 400 and 600 Hz, and these results are similar to those measured by MRE in some previous studies. Although 400 and 600 Hz are not frequencies typically used for MRE evaluation, using lower frequency may be possible when using extended FOV of curvilinear transducers.

The amplitude of the tissue motion at the focal point is used as an indication of the tissue elasticity (i.e., smaller motion amplitudes are observed in stiffer portion of the tissue). HSWI can produce equivalent measurements to THI if the focal point is located inside the ROI. The measurement results by HSWI were compared to those measured by SSI.

These observations suggest that HSWI is a versatile technique that can be used for clinical implementation of other well-known harmonic methods.

HSWI may be implemented on commercial ultrasound scanners and used in clinical practice. HSWI could also be applied to the differential diagnosis of benign and malignant thyroid nodules, and the evaluation of the stiffness of muscles.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A method of performing shear wave elastography in tissue, comprising:
providing a single array transducer;
transmitting successively a series of ultrasound push pulses in the tissue around a region of interest (ROI) using the single array transducer, acoustic intensities of the push pulses being sinusoidally modulated to follow a sinusoidally changing pattern with a sinusoidal modulation frequency;
each push pulse generating an acoustic radiation force that pushes the tissue thus creating an individual shear wave having an amplitude and propagating through the tissue, the amplitude of each individual shear wave changing positively proportionally to the intensities of the push pulses, the successively created individual shear waves with different amplitudes summing together to form a continuous, narrowband summed shear wave with a single frequency, the single frequency being the same as the sinusoidal modulation frequency of the push pulses.

2. The method according to claim 1, further comprising:
transmitting imaging pulses using the single array transducer between the push pulses; and
imaging/detecting the continuous, narrowband summed shear wave.

3. The method according to claim 2, wherein imaging/detecting the continuous, narrowband summed shear wave comprises generating maps of shear wave speed or shear modulus using the imaging pulses.

4. The method according to claim 3, wherein the maps generated are 2D field-of-view (FOV) maps.

5. The method according to claim 2, wherein part of elements of the single array transducer are used to transmit the imaging pulses.

6. The method according to claim 2, wherein the imaging pulses are plane wave pulses.

7. The method according to claim 2, wherein at least two image pulses are transmitted between two subsequent push pulses.

8. The method according to claim 2, wherein compounding plane wave pulses with three angles of $-15°$, $0°$ and $15°$ are used.

9. The method according to claim 1, wherein the single array transducer is a linear, 1.5D, or 2D array transducer.

10. The method according to claim 1, wherein the intensities of the push pulses are modulated by changing magnitudes of a applied voltage, pulse durations, or aperture sizes of the transducer.

11. The method according to claim 1, wherein the push pulses are transmitted at a focal position adjacent the ROI.

12. The method according to claim 1, wherein at least two push pulses are transmitted per cycle.

13. The method according to claim 1, wherein at least four push pulses are transmitted per cycle.

14. The method according to claim 1, wherein a lower limit of the frequency is chosen such that at least two wavelengths are in the ROI.

* * * * *